United States Patent [19]

Atkins et al.

[11] Patent Number: 5,112,784

[45] Date of Patent: May 12, 1992

[54] PROCESS FOR THE PREPARATION OF CATALYSTS

[75] Inventors: Martin P. Atkins, Sunbury-on-Thames; William Jones, Cambridge; Malama Chibwe, Romford, all of England

[73] Assignee: The British Petroleum Company p.l.c., London, England

[21] Appl. No.: 586,825

[22] Filed: Sep. 24, 1990

[30] Foreign Application Priority Data

Oct. 4, 1989 [GB] United Kingdom ................ 8922359

[51] Int. Cl.$^5$ ............................................. B01J 21/16
[52] U.S. Cl. .................................................... 502/80
[58] Field of Search ......................................... 502/80

[56] References Cited

U.S. PATENT DOCUMENTS

| 3,226,252 | 12/1965 | Hemstock | 502/80 |
| 4,444,899 | 4/1984 | Yamada et al. | 502/80 |
| 4,458,026 | 7/1984 | Reichle | 502/80 |
| 4,601,997 | 7/1986 | Speronello | 502/80 |

Primary Examiner—Carl F. Dees
Attorney, Agent, or Firm—Larry W. Evans; Joseph G. Curatolo; Sue E. Phillips

[57] ABSTRACT

A process for the preparation of a catalytically active material, which comprises calcining an anionic double hydroxide clay; rehydrating the resulting material by treatment with water substantially free from dissolved ions; and calcining the rehydrated material.

8 Claims, 2 Drawing Sheets

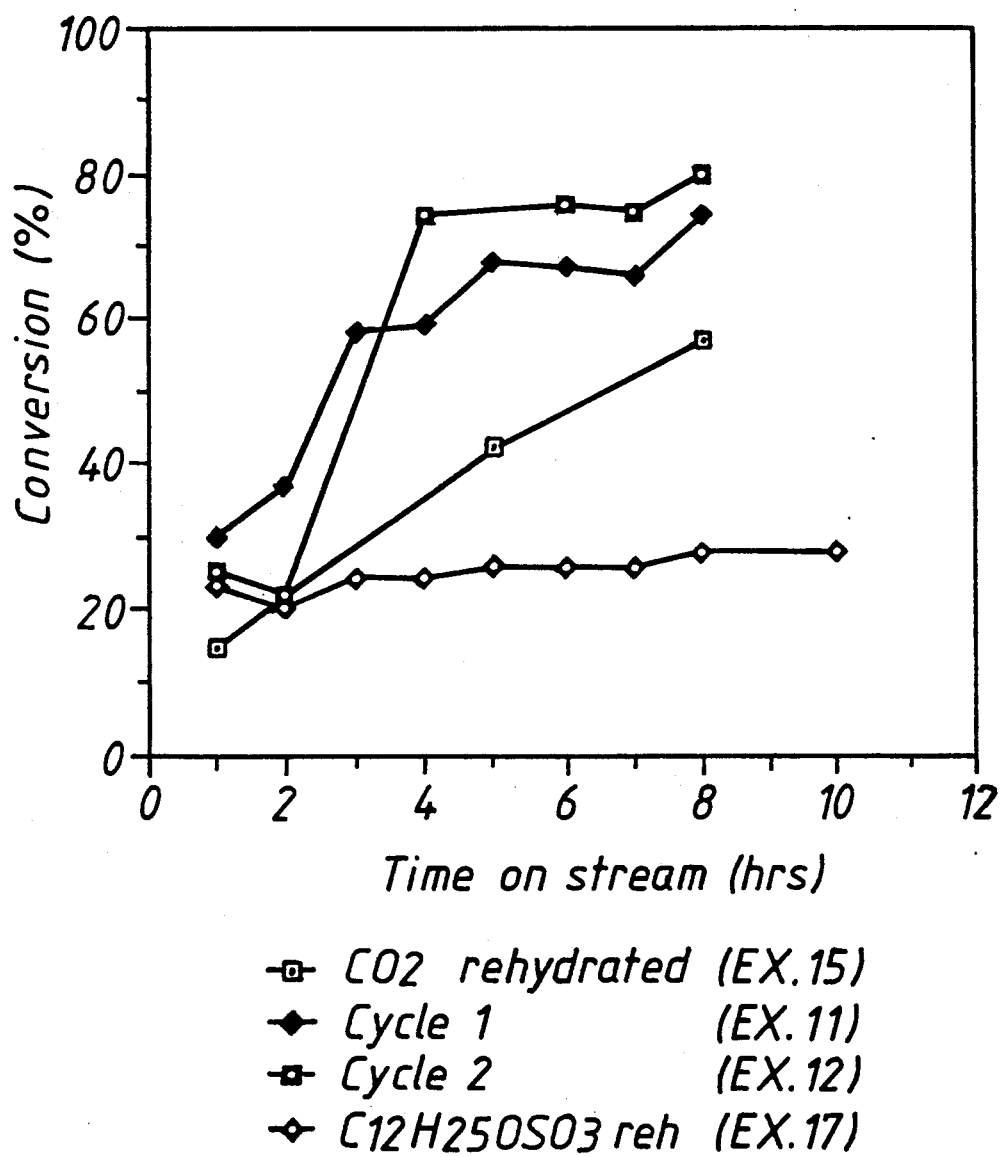

PROCESS FOR THE PREPARATION OF CATALYSTS

This invention relates to a process for the preparation of catalysts.

Anionic double hydroxide clays are well-known materials. They are described in, for example, "Anionic Clay Minerals", W. T. Reichle, "Chemtec", Jan. 1986. They consist of positively charged metal oxide/hydroxide sheets with intercalated anions and water molecules. In terms of charge they are mirror-images of the much studies family of cationic clay minerals. The structure of anionic double hydroxide clays is related to that of brucite, $Mg(OH)_2$. In brucite magnesium is octahedrally surrounded by six oxygens in the form of hydroxide; the octahedral units then, through edge sharing, form infinite sheets. The sheets are stacked on top of each other by hydrogen bonds. If some of the magnesium in the lattice is isomorphously replaced by a higher charged cation, e.g. $Al^{3+}$, then the resulting overall single $Mg^{2+}$-$Al^{3+}$-OH layer gains a positive charge. Sorption of an equivalent amount of hydrated anions renders the structure electrically neutral, resulting in an anionic double hydroxide clay.

Anionic double hydroxide clays have, in the dehydrated form, the empirical formula:

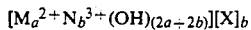

in which $M^{2+}$ is a divalent metal cation; $N^{3+}$ is a trivalent metal cation; X is one equivalent of an anion; and a and b represent the relative proportions of M and N in the structure. Typically, $M^{2+}$ is $Mg^{2+}$, $Fe^{2+}$, $Co^{2+}$ and/or $Zn^{2+}$, and $N^{3+}$ is $Al^{3+}$, $Cr^{3+}$ and/or $Fe^{3+}$. In an alternative form, the divalent metal may be wholly or partly replaced by lithium, the all-lithium form having the empirical formula:

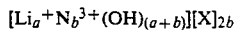

In the naturally-occurring minerals hydrotalcite and mannaseite, $M^{2+}$ is $Mg^{2+}$, $N^{3+}$ is $Al^{3+}$, X is carbonate, and a/b is in the range of 1:1 to 5:1. Such minerals occur in a hydrated form.

U.S. Pat. No. 4,458,026 discloses that catalysts prepared by calcination of anionic double hydroxide clays may be used to perform aldol condensations.

We have now found that catalytic activity of materials prepared by calcination of anionic double hydroxide clays can be enhanced by a specific rehydration-recalcination treatment.

BRIEF DESCRIPTION OF THE DRAWINGS

FIG. 2 is a graph summarizing the conversion data from Examples 11, 12, 15 and 17.

Figure 1:
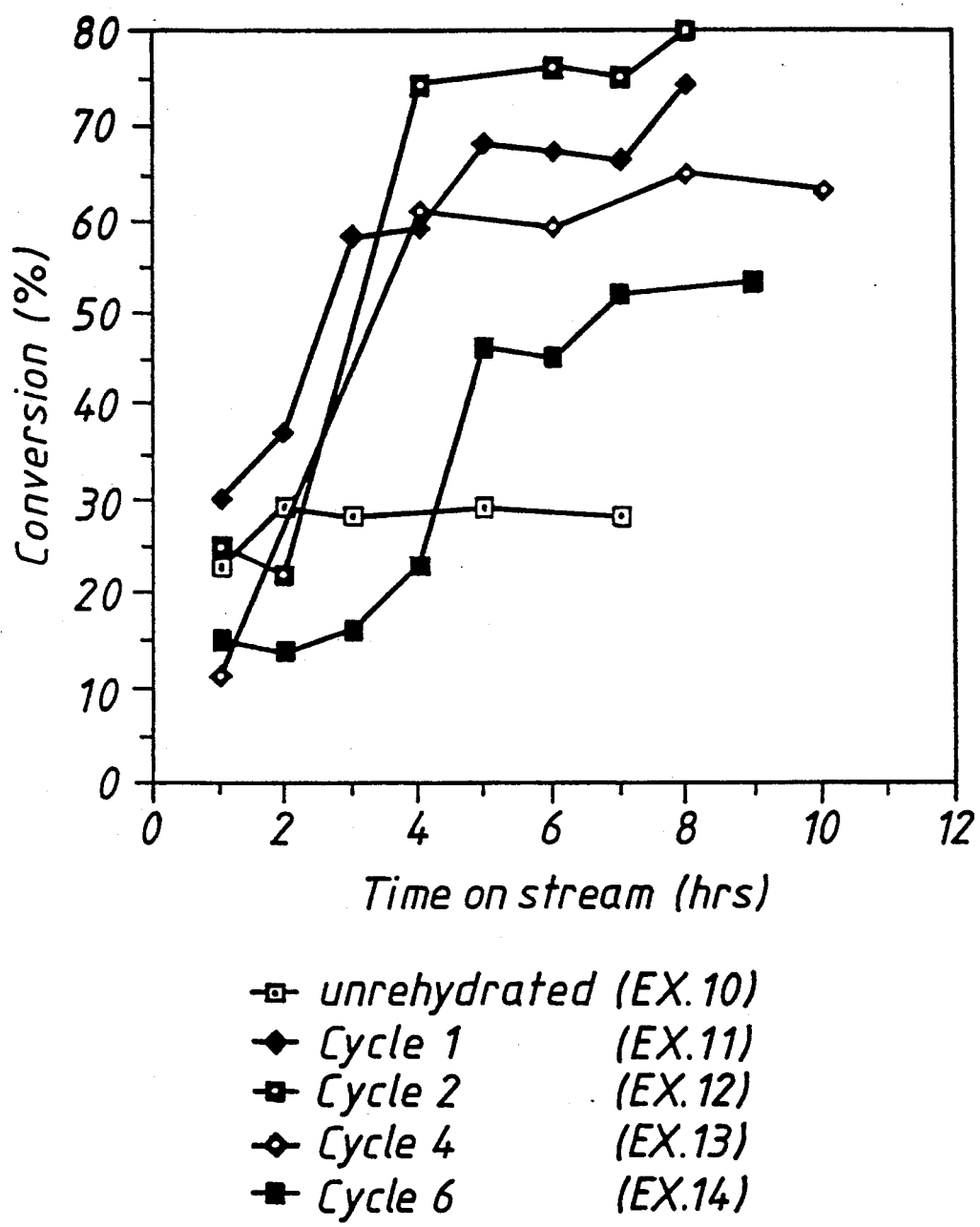
FIG. 1 is a graph summarizing the conversion data from Examples 10, 11, 12, 13 and 14.

Accordingly, the present invention provides a process for the preparation of a catalytically active material, which comprises calcining an anionic double hydroxide clay; rehydrating the resulting material by treatment with water substantially free from dissolved ions; and calcining the rehydrated material.

Anionic double hydroxide clays can be prepared by known methods, for example by the method described in U.S. Pat. No. 4,458,026. In general, solutions of soluble salts of the relevant metals are mixed together with an alkali metal hydroxide and an alkali metal carbonate. The resulting mixture is vigorously stirred until a slurry is formed. The slurry is then heated, typically to a temperature between 50° and 100° C., preferably 60° to 75° C., until sufficient crystallisation occurs.

In order to prepare a catalytically active material by the process of the invention, an anionic double hydroxide clay is subjected to calcination. Preferably this involves heating to a temperature of at least 300° C., preferably 300° to 550° C., especially 400° to 500° C., under non-reducing conditions. The heating may be carried out under vacuum, in an inert gas or, preferably, in an oxidising atmosphere, preferably air. Heating is carried out for a period of time typically between 10 and 30 hours. Such treatment causes the collapse of the double hydroxide layered structure, and, generally, results in an oxide material having a structure related to that of MgO.

The resulting material is then rehydrated by treatment with water substantially free from dissolved ions, particularly decarbonated water. Suitable decarbonated water may be prepared by purging distilled or deionised water with an inert gas, for example nitrogen, argon or hydrogen, to remove carbon dioxide and hence carbonate ions. Rehydration may be carried out simply by soaking for an adequate period of time, typically from 10 to 30 hours. The material is then calcined by the same method as used for the initial calcination. Such rehydration/recalcination treatment may be repeated, if desired a number of times, with beneficial results, especially when using a material containing magnesium and aluminium.

The catalytically active material prepared by the process according to the invention, may be used to carry out a number of reactions. It may for example be used in the preparation of a glycol ether by reacting an olefin oxide with an alcohol over a catalyst. Typically, ethanol is reacted with propylene oxide to product a mixture of the primary or secondary glycol ethers, 2-ehtoxy-1-propanol and 1-ethoxy-2-propanol. It is a major advantage of materials prepared by the process of the invention that they are able to carry out this reaction with a high selectivity to the secondary product, which is in general the desired product.

the following Examples illustrate the invention. Example 1 illustrates the synthesis of an anionic double hydroxide clay; Examples 2 to 9 illustrate treatment of anionic double hydroxide clays to produce catalysts; and Examples 10 to 17 illustrate the use of these catalysts in the production of glycol ethers. Examples 9, 10, 16 and 17 are comparative, not according to the invention.

EXAMPLE 1

Preparation of a Magnesium/Aluminium/Carbonate Anionic Double Hydroxide Clay A solution of 256 g $(Mg(NO_3)_2.6H_2O$ (1.00 mole) and 187.5 g $Al(NO_3)_3.9H_2O$ (0.50 moles) in 700 ml deionised water was added dropwise to a solution of 140 g NaOH (3.5 mole) and 100 g anhydrous $Na_2CO_3$ (0.943 mole) in 1000 ml deionised water. The addition was carried out in a 3 liter flask and uniform mixing was achieved by use of a mechanical stirrer. Using a cooling bath, the temperature was maintained at about 35° C. during addition which took about 4 hours. A heavy slurry was formed. The flask contents were then transferred to a thermal bath and heated to and maintained at 65°±2° C. for 18 hours with continuous stirring. Thereafter the resulting thick slurry was filtered and washed with a large excess of deionised water. The sold was then dried at 125° C. either in vacuum or air for 18 hours. The resulting white powder gave an X-ray powder diffraction profile of hydrotalcite. This XRD profile is given in Table XRD-1.

Elemental analysis: 11.99% Al; 19.08% Mg; 2.60% C. This corresponds to an empirical formula of $Mg_6Al_{3.3}(OH)_{18.6}(CO_3)_{1.7}4H.O$.

$^{27}Al$ magic angle spinning nmr gave a single peak of chemical shift 8.3 ppm, corresponding to all the aluminum being in octahedral coordination.

EXAMPLE 2

Calcination

The product of Example 1 was calcined at 450° C. for 18 hours in air. The resulting catalyst had a surface area of 180 $m^2/g$, and an elemental analysis of 16.87% Al and 27.3% Mg.

$^{27}Al$ nmr after calcination showed peaks at 77.1 ppm and 11.5 ppm, corresponding to tetrahedrally and octahedrally coordinated aluminium. The XRD profile is given in Table XRD-2.

EXAMPLE 3

First Cycle Rehydration 10.0 g of the calcined material prepared as in Example 2 was taken and added to 100 ml previously boiled water and cooled with bubbling $N_2$ for about an hour. The material was then left overnight. It was then washed with hot distilled water and partially dried under $N_2$ before being dried at 125° C. This material gave the XRD pattern of a regenerated anionic double hydroxide (hereafter referred to as regenerated 1st cycle) and the reflections are shown in Table XRD-3. The material was then calcined at 450° C. for 18 hours to generate the catalyst. The XRD pattern, given in Table XRD-4, showed two phases: a relatively small amount of spinel and the expected pattern of a collapsed anionic double hydroxide clay, i.e. MgO structure.

EXAMPLE 4

Second Cycle Rehydration

Example 3 was repeated using as starting material the product of Example 3. The XRD powder pattern of the rehydrated material is shown in Table XRD-5, and that of the rehydrated recalcinated material in Table XRD-6.

EXAMPLE 5

Example 3 was repeated using as starting material the product of Example 4.

EXAMPLE 6

Fourth Cycle Rehydration

Example 3 was repeated using as starting material the product of Example 5. The resulting calcined material had the XRD pattern shown in Table XRD-7, and had $^{27}Al$ nmr peaks at 67.6 and 11.0 ppm.

EXAMPLE 7

Fifth Cycle Rehydration

Example 3 was repeated using as starting material the product of Example 8

Sixth Cycle Rehydration

Example 3 was repeated using as starting material the product of Example 7.

COMPARATIVE EXAMPLE 9

Example 3 was repeated but this time carbon dioxide was bubbled through undecarbonated distilled water. The XRD pattern was that of a regenerated anionic double hydroxide clay. Carbonate was confirmed to be the interlayer anion from fourier transform i.r. and microanalysis of carbon.

COMPARATIVE EXAMPLE 10

Example 3 was repeated using a 0.1 M solution of sodium dodecyl sulphate ($C_{12}H_{25}OSO_3Na$) and 10 g of the calcined precursor of the parent material by heating at 450° C. for 18 hours in air. The calcined precursor was in powder form. The product revealed some regenerated anionic double hydroxide clay in expanded form due to the intercalated organic guest. The phase due to carbonate interference was also present as confirmed by fourier transform i.r. and XRD.

EXAMPLE 11 TO 17

Preparation of glycol ethers

Tests were carried out in a fixed bed continuous flow reactor. A 10 $dm^3$ feed pot contained the reactants which were pumped through the 316 stainless steel reactor (¼"OD) under applied nitrogen pressure and containing pelleted catalyst. Two 1/16" thermocouples went on sides of the reactor right through to the centre of the catalyst bed. The product was collected in an ice-cooled vial and analysed immediately on a Perkin Elmer gas chromatograph equipped with a temperature programming facility. The injection port was held at 150° C. with the hot wire detector at 150° C. Helium carrier gas flowed at 25 ml/min. The column used was 5 meters×⅛ inch O.D. stainless steel column packed with 10% carbowax 20 M on 60–80 mesh chromosorb was temperature programmed at 60° C. for 6 minutes and then 12° C./min to 180° C.

EXAMPLE 11

Starting reactant mole ratio ethanol/propylene oxide 10/1. Catalyst: product of Example 2; ;weight-6.5 g, volume-10 ml, temperature-122°±1° C., feed rate-21 ml/hr, pressure-15 bar.

The results are given in Table A(1). 2° refers to the secondary glycol ether, 1-ethoxy-2-propanol, and 1° refers to the primary glycol ether, 2-ethoxy-1-propanol. Secondary product selectivity is defined as $2°/(2°+1°)(\%)$.

TABLE A(1)

| | Results of Example 11 | |
|---|---|---|
| Time on stream (hours) | % conversion of propylene oxide | 2° product selectivity |
| 1 | 23 | 94 |
| 2 | 29 | 94 |
| 3 | 28 | 94 |
| 5 | 28 | 93 |
| 7 | 28 | 92 |

EXAMPLE 12

The calcined material of Example 3 was tested: weight-6.7 g, volume-9 ml, temperature-120° C., feed rate-10.5 ml/hr, pressure-15 bar. The results are given in Table 1.

TABLE 1

Results of Example 12

| Time on stream (hours) | % conversion of propylene oxide | 2° product selectivity |
|---|---|---|
| 1 | 30 | 83 |
| 2 | 37 | 95 |
| 3 | 58 | 86 |
| 4 | 59 | 89 |
| 5 | 68 | 88 |
| 6 | 67 | 93 |
| 7 | 66 | 90 |
| 8 | 74 | 88 |

EXAMPLE 13

The calcined material obtained in Example 4 was tested. Weight-4.4 g, volume-6 ml, temperature-120° C., feed rate-7.2 ml/hr, pressure-15 bar. The results are given in Table 2.

TABLE 2

Results of Example 13

| Time on stream (hours) | % conversion of propylene oxide | 2° product selectivity |
|---|---|---|
| 1 | 25 | 100 |
| 4 | 74 | 84 |
| 6 | 76 | 84 |
| 8 | 76 | 88 |
| 10 | 75 | 81 |
| 13 | 80 | 84 |

EXAMPLE 14

The calcined material obtained in Example 6 was tested. Weight-5.4 g, volume-5 ml, temperature-120° C., feed rate-7.5 ml/hr, pressure-15 bar. The results are given in Table 3.

TABLE 3

Results of Example 14

| Time on stream (hours) | % conversion of propylene oxide | 2° product selectivity |
|---|---|---|
| 1 | 11 | 100 |
| 4 | 61 | 85 |
| 6 | 59 | 85 |
| 8 | 65 | 83 |
| 10 | 63 | 89 |

EXAMPLE 15

The calcined material obtained in Example 8 was tested. Weight-7.3 g, volume-10 ml, temperature-120° C., feed rate-15 ml, pressure-15 bar. The results are given in Table 4.

TABLE 4

Results of Example 15

| Time on stream (hours) | % conversion of propylene oxide | 2° product selectivity |
|---|---|---|
| 1 | 15 | 87 |
| 2 | 14 | 87 |
| 3 | 16 | 86 |
| 4 | 23 | 88 |
| 5 | 46 | 89 |
| 6 | 45 | 88 |
| 7 | 52 | 87 |
| 9 | 53 | 86 |

COMPARATIVE EXAMPLE 16

The calcined material obtained in Comparative Example 9 was tested. Weight-6.2 g, volume-9 ml, temperature-120° C., feed rate-10.5 ml/hr, pressure-15 bar. The results are given in Table 5.

TABLE 5

Results of Comparative Example 16

| Time on stream (hours) | % conversion of propylene oxide | 2° product selectivity |
|---|---|---|
| 2 | 15 | 89 |
| 5 | 42 | 82 |
| 8 | 57 | 86 |

COMPARATIVE EXAMPLE 17

The calcined material of comparative Example 10 was tested. Weight-4.75 g, volume-10 ml, temperature-122°±2° C., feed rate-15 ml/hr, pressure-15 bar. The results are given in Table 6.

TABLE 6

Results of Comparative Example 17

| Time on stream (hours) | % conversion of propylene oxide | 2° product selectivity |
|---|---|---|
| 1 | 23 | 52 |
| 2 | 20 | 67 |
| 3 | 24 | 66 |
| 4 | 24 | 73 |
| 5 | 26 | 70 |
| 6 | 26 | 83 |
| 7 | 28 | 80 |
| 9 | 28 | 75 |

In the following tables of X-ray diffraction data, VS=very strong, S=strong, FS=fairly strong, M=medium, W=weak, VW=very weak and B=broad.

TABLE XRD-1

Powder X-ray diffraction data for uncalcined sample from Example 1

| d/Å | Relative Intensity ($I/I_o$) |
|---|---|
| 7.8 | VS |
| 3.9 | S |
| 2.6 | S |
| 2.3 | W |
| 1.9 | W |
| 1.53 | S |
| 1.50 | FS |

TABLE XRD-2

Powder X-ray diffraction data for calcined sample from Example 2

| d/Å | Relative Intensity ($I/I_o$) |
|---|---|
| 2.6 | BW |
| 2.1 | S |
| 1.5 | FS |
| 1.2 | W |

TABLE XRD-3

Powder X-ray diffraction data for rehydrated sample from Example 3

| d/Å | Relative Intensity ($I/I_o$) |
|---|---|
| 7.8 | VS |
| 3.9 | S |
| 2.6 | S |
| 2.3 | W |
| 1.9 | W |

TABLE XRD-3-continued

Powder X-ray diffraction data for rehydrated sample from Example 3

| d/Å | Relative Intensity (I/I$_o$) |
|---|---|
| 1.53 | S |
| 1.50 | FS |

TABLE XRD-4

Powder X-ray diffraction data for calcined sample from product in Example 3. Starred (*) values due to spinel (MgAl$_2$O$_4$) and the unstarred due to anionic double hydroxide clay.

| d/Å | Relative Intensity (I/I$_o$) |
|---|---|
| 2.4* | W |
| 2.1 | S |
| 2.0* | FS |
| 1.6* | W |
| 1.5 | FS |
| 1.4* | FS |

TABLE XRD-5

Powder X-ray diffraction data for rehydrated sample from Example 4. Starred (*) values due to spinel (MgAl$_2$O$_4$) and the unstarred due to anionic double hydroxide clay.

| d/Å | Relative Intensity (I/I$_o$) |
|---|---|
| 7.8 | VS |
| 3.9 | S |
| 2.6 | S |
| 2.4* | W |
| 2.3 | FS |
| 2.02* | W |
| 1.98 | W |
| 1.53 | FS |
| 1.50 | S |
| 1.4* | FS |

TABLE XRD-6

Powder X-ray diffraction data for calcined sample from Example 4. Starred (*) values due to spinel (MgAl$_2$O$_4$) and the unstarred due to anionic double hydroxide clay.

| d/Å | Relative Intensity (I/I$_o$) |
|---|---|
| 4.7* | W |
| 2.8* | W |
| 2.4* | FS |
| 2.1 | S |
| 2.0* | S |
| 1.6* | S |
| 1.5 | S |

TABLE XRD-7

Powder X-ray diffraction data for calcined product in Example 8. Starred (*) values due to spinel and the unstarred due to anionic double hydroxide clay.

| d/Å | Relative Intensity (I/I$_o$) |
|---|---|
| 4.7* | W |
| 2.9* | W |
| 2.4* | S |
| 2.1 | S |
| 2.0* | S |
| 1.6* | VW |
| 1.5 | W |
| 1.4* | S |

We claim:

1. A process for the preparation of a catalytically active material, which comprises calcining an anionic double hydroxide clay; rehydrating the resulting material by treatment with water substantially free from dissolved ions; and calcining the rehydrated material.

2. A process as claimed in claim 1, in which calcination is carried out by heating to a temperature of from 300° to 550° C. under non-reducing conditions.

3. A process as claimed in claim 2, in which calcination is carried out by heating in air.

4. A process as claimed in claim 2, in which the rehydration/recalcination treatment is repeated.

5. A process as claimed in claim 2, in which the catalytically active material contains magnesium and aluminium.

6. A process as claimed in claim 3 in which the rehydration/recalcination treatment is repeated.

7. A process as claimed in claim 3 in which the catalytically active material contains magnesium and aluminum.

8. A process as claimed in claim 4 in which the catalytically active material contains magnesium and aluminium.

* * * * *